United States Patent
Gauriau et al.

(10) Patent No.: US 11,282,170 B2
(45) Date of Patent: Mar. 22, 2022

(54) CONTRAST INJECTION IMAGING

(71) Applicant: KONINKLIJKE PHILIPS N.V., Eindhoven (NL)

(72) Inventors: Romane Isabelle Marie-Bernard Gauriau, Paris (FR); Christian Haase, Hamburg (DE); Michael Grass, Buchholz In der Nordheide (DE); Javier Olivan Bescos, Eindhoven (NL); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 16/496,620

(22) PCT Filed: Mar. 29, 2018

(86) PCT No.: PCT/EP2018/058152
§ 371 (c)(1),
(2) Date: Sep. 23, 2019

(87) PCT Pub. No.: WO2018/178272
PCT Pub. Date: Oct. 4, 2018

(65) Prior Publication Data
US 2020/0020079 A1    Jan. 16, 2020

(30) Foreign Application Priority Data
Mar. 30, 2017   (EP) ..................... 17305369

(51) Int. Cl.
G06T 3/40      (2006.01)
G06T 17/00     (2006.01)
A61B 5/026     (2006.01)
A61B 6/00      (2006.01)

(52) U.S. Cl.
CPC ............ G06T 3/4061 (2013.01); G06T 17/00 (2013.01); *A61B 5/0263* (2013.01); *A61B 6/481* (2013.01); *A61B 6/504* (2013.01); *A61B 6/5235* (2013.01)

(58) Field of Classification Search
CPC ..... A61B 5/0263; A61B 6/504; A61B 6/5235; G06T 17/00; G06T 3/4061
See application file for complete search history.

(56) References Cited

U.S. PATENT DOCUMENTS

| 6,389,104 B1 | 5/2002 | Bani-Hashemi |
| 7,689,019 B2 | 3/2010 | Boese |
| 2007/0116342 A1 | 5/2007 | Zarkh |

(Continued)

FOREIGN PATENT DOCUMENTS

WO    2009081297 A2    7/2009

OTHER PUBLICATIONS

International Search Report & Written Opinion of PCT/EP2018/058152, dated Jun. 14, 2018.

(Continued)

*Primary Examiner* — Manuchehr Rahmjoo

(57) ABSTRACT

Vasculature modeling systems and methods are disclosed that generate an enhanced 3D model based on a combination of two dimensional, 2D, imaging data of a region of interest and 3D imaging data of the region of interest. A hemodynamic simulation is performed using the enhanced 3D model to derive at least one hemodynamic parameter based on the hemodynamic simulation.

12 Claims, 4 Drawing Sheets

(56) References Cited

U.S. PATENT DOCUMENTS

| | | | |
|---|---|---|---|
| 2011/0037761 A1 | 2/2011 | Mistretta | |
| 2012/0230558 A1 | 9/2012 | Chen | |
| 2015/0065864 A1 | 3/2015 | Sharma | |
| 2015/0342551 A1 | 12/2015 | Lavi | |
| 2015/0356753 A1* | 12/2015 | Lauritsch | G06T 7/20 382/130 |

OTHER PUBLICATIONS

Lesage, D et al "A review of 3D Vessel Lumen Segmentation techniques: Models, features and extraction schemes", Medical Image Analysis, vol. 13, No. 6, pp. 819-845, 2009.
Zhang, Jun-Mei et al "Numerical Simulation and Clinical Implications of Stenosis in Coronary Blood flow", Biomed Research International, vol. 2014, Article ID 514729, 2014.
Markelj, et al A review of 3D/2D registration methods for image-guided interventions, Medical Image Analysis, vol. 16, No. 3, pp. 642-661, 2012.
Son, Jinwon et al "Reconstruction of Intima and Adventitia Models into a State Undeformed by a Catheter by using CT, IVUS, and Biplane X-Ray Angiogram Images" Computational and Mathematical Methods in Medicine, vol. 2017, Jan. 2017, pp. 1-13.
Mitrovi, Uro et al "Method for 3D-2D Registration of Vascular Images: Application to 3D Contrast Agent Flow Visualization", Clinical Image-Based Procedures. From Planning to Intervention, vol. 7761, Oct. 2012, pp. 50-58.
Langs, Georg et al "Building and registering parameterized 3D Models of Vessel Trees for Visualization during Intervention", Proceedings of the 17th International Conf. on Pattern Recognition, 2004.

* cited by examiner

CONTRAST INJECTION IMAGING

CROSS-REFERENCE TO PRIOR APPLICATIONS

This application is the U.S. National Phase application under 35 U.S.C. § 371 of International Application No. PCT/EP2018/058152, filed on Mar. 29, 2018, which claims the benefit of European Patent Application No. 17305369.5, filed on Mar. 30, 2017. These applications are hereby incorporated by reference herein.

FIELD OF THE INVENTION

The technical field generally relates to vasculature modeling. In particular, the technical field relates to assessing disease of the vasculature through hemodynamic simulation of a vasculature model.

BACKGROUND OF THE INVENTION

US2015065864 discloses a method and system for non-invasive functional assessment of renal artery stenosis. A non-invasive method for computing the functional and anatomical severity of a renal artery stenosis by using medical image data and flow simulations. One or more hemodynamic quantities are calculated for the renal artery stenosis based on blood flow simulations. The blood flow simulations include a step of calculating inflow and outflow in the renal artery. In order to quantify the flow in the renal arteries, a patient-specific anatomical model of the renal arteries and aorta is used to mask the flow image data in order to obtain the flow information in the lumen.

In US2015065864, a patient-specific anatomical model of the renal arteries and aorta is extracted from the medical image data. To do so, the renal arteries can be segmented in three-dimensional, 3D, medical image data using an automated renal artery centerline extraction algorithm. Once the renal artery centerlines are extracted, cross-section contours can be generated at each point of the centerlines. The cross-section contour at each centerline point gives a corresponding cross-section area measurement at that point in the coronary artery.

Accuracy of the geometric artery models is of significant importance for a reliable outcome of hemodynamic simulations and other diagnostic algorithms. Whilst the 3D model offers information on cross-sectional shape and position in 3D space, 3D imaging can lack accuracy in terms of spatial resolution.

Thus, it is desired to provide a vasculature modeling system and method having enhanced accuracy vasculature model. It is further desirable to provide an enhanced accuracy vasculature model allows more realistic hemodynamic values to be derived from a hemodynamic simulation.

SUMMARY OF THE INVENTION

Hence, there may be a need to provide an improved and facilitated way of vasculature modeling.

Generally, the present invention proposes to provide vasculature modeling systems and methods that generate an enhanced 3D model based on a combination of two dimensional, 2D, imaging data of a region of interest and 3D imaging data of the region of interest. For example, the 2D imaging data generally has higher spatial resolution but lacks 3D spatial information, and the 3D imaging data has 3D spatial information, but, generally, lower spatial resolution. The combination may involve a registration of the 2D imaging data and the 3D imaging data and/or a registration of at least one feature derived from the 2D imaging data with at least one corresponding feature derived from the 3D imaging data. For example, the feature is a feature of the vasculature, such as a vessel centerline.

Building an enhanced model based on a combination of features of both 3D and 2D imaging data may lead to a more accurate geometric description of the vessel anatomy.

The object of the present invention is solved by the subject-matter of the independent claims; wherein further embodiments are incorporated in the dependent claims. It should be noted that the following described aspects of the invention apply also for the image processing system, for the imaging system, for the medical system and for the computer implemented method as well as for the computer program element and the computer readable medium.

In one embodiment, a vasculature modeling system is provided. The system includes a data receiver configured to receive two dimensional, 2D, imaging data including a region of interest of vasculature and three dimensional, 3D, imaging data of the region of interest. An image processing system is configured to generate an enhanced 3D model of the region of interest based on a combination of the 3D imaging data and the 2D imaging data.

In embodiments, a spatial resolution of the 2D imaging data is greater than a spatial resolution of the 3D imaging data. In this way, the enhanced 3D model is able to incorporate the higher spatial resolution of the 2D imaging data.

In embodiments, the image processing system is configured to generate the enhanced 3D model of the region of interest based on vessel diameter data derived from the 2D imaging data. Due to the generally higher spatial resolution of the 2D imaging data, diameter (or equivalently radius) data derived from the 2D imaging data can have greater accuracy.

In embodiments, the image processing system is configured to generate the enhanced 3D model of the region of interest based on vessel cross-sectional shape data derived from the 3D imaging data. Cross-sectional shape is data that is more accurately derivable from the 3D imaging data. Further, cross-sectional area data is more accurately derivable from the cross-sectional shape.

In embodiments, the image processing system is configured to generate the enhanced 3D model of the region of interest based on vessel centerline data derived from the 3D imaging data. The vessel centerline extends in 3D space in the 3D imaging data and thus is more accurate than 2D centerline data that extends along a 2D plane.

In embodiments, the image processing system is configured to generate the enhanced 3D model of the region of interest having a spatial resolution of the 2D imaging data. The spatial resolution of the 2D imaging data is generally greater than that of the 3D imaging data, thereby providing a more accurate 3D model.

In embodiments, the image processing system is configured to generate the enhanced 3D model of the region of interest by combining the 3D imaging data and the 2D imaging data using an image registration and image deformation technique including terms to maintain, in the enhanced 3D model, at least one of: vessel centerline derived from the 3D imaging data; cross-sectional shape derived from the 3D imaging data; spatial resolution derived from the 2D imaging data; and vessel diameter derived from the 2D imaging data.

In embodiments, the 3D imaging data is magnetic resonance imaging, MRI, imaging data or computed tomography, CT, imaging data and/or the 2D imaging data is X-ray angiogram imaging data.

In embodiments, the system includes a hemodynamic simulator configured to perform a hemodynamic simulation using the enhanced 3D model and to derive at least one hemodynamic parameter based on the hemodynamic simulation. In particular, the hemodynamic simulation is based on at least one values for: vessel centerline derived from the 3D imaging data; cross-sectional shape derived from the 3D imaging data; spatial resolution derived from the 2D imaging data; and vessel diameter derived from the 2D imaging data as incorporated into the enhanced 3D model.

In embodiments, the image processing system is configured to build a quasi 3D model based on vessel centerline data derived and vessel diameter data derived from the 2D imaging data. The image processing system is configured to generate the enhanced 3D model based on a 3D to 3D registration and deformation process on the quasi 3D model and a 3D model derived from the 3D imaging data. For example, vessel centerline data of the quasi 3D model, as derived from the 2D imaging data, is registered to the vessel centerline data of the 3D model, as derived from the 3D imaging data, and transformed accordingly.

In other embodiments, the imaging processing system is configured to perform 2D to 3D image registration process based on the 2D imaging data and the 3D imaging data to produce registered 2D and 3D imaging data and to perform an image deformation process based on the registered 2D and 3D imaging data. In embodiments, the 2D to 3D image registration process is performed on the 3D and 2D imaging data, 3D and 2D vessel models are generated based respectively on the registered 3D and 2D imaging data and the image deformation process is performed based on the 3D and 2D vessel models that are registered to one another.

In another embodiment, a computer implemented method for vasculature modeling is provided. The method includes receiving two dimensional, 2D, imaging data including a region of interest of vasculature and three dimensional, 3D, imaging data of the region of interest. The method includes generating an enhanced 3D model of the region of interest based on a combination of the 3D imaging data and the 2D imaging data.

The features describe above with respect to the modeling system are applicable to the computer implemented method.

In yet another embodiment, a computer program element is provided that is adapted to implement an image processing system as described herein or adapted to perform the computer implemented method steps described herein when executed by at least one processor.

A computer readable medium is also provided having stored thereon, the computer program element.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

The following detailed description is merely exemplary in nature and is not intended to limit the application and uses. Furthermore, there is no intention to be bound by any expressed or implied theory presented in the preceding technical field, background, brief summary or the following detailed description.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

Figure 1:
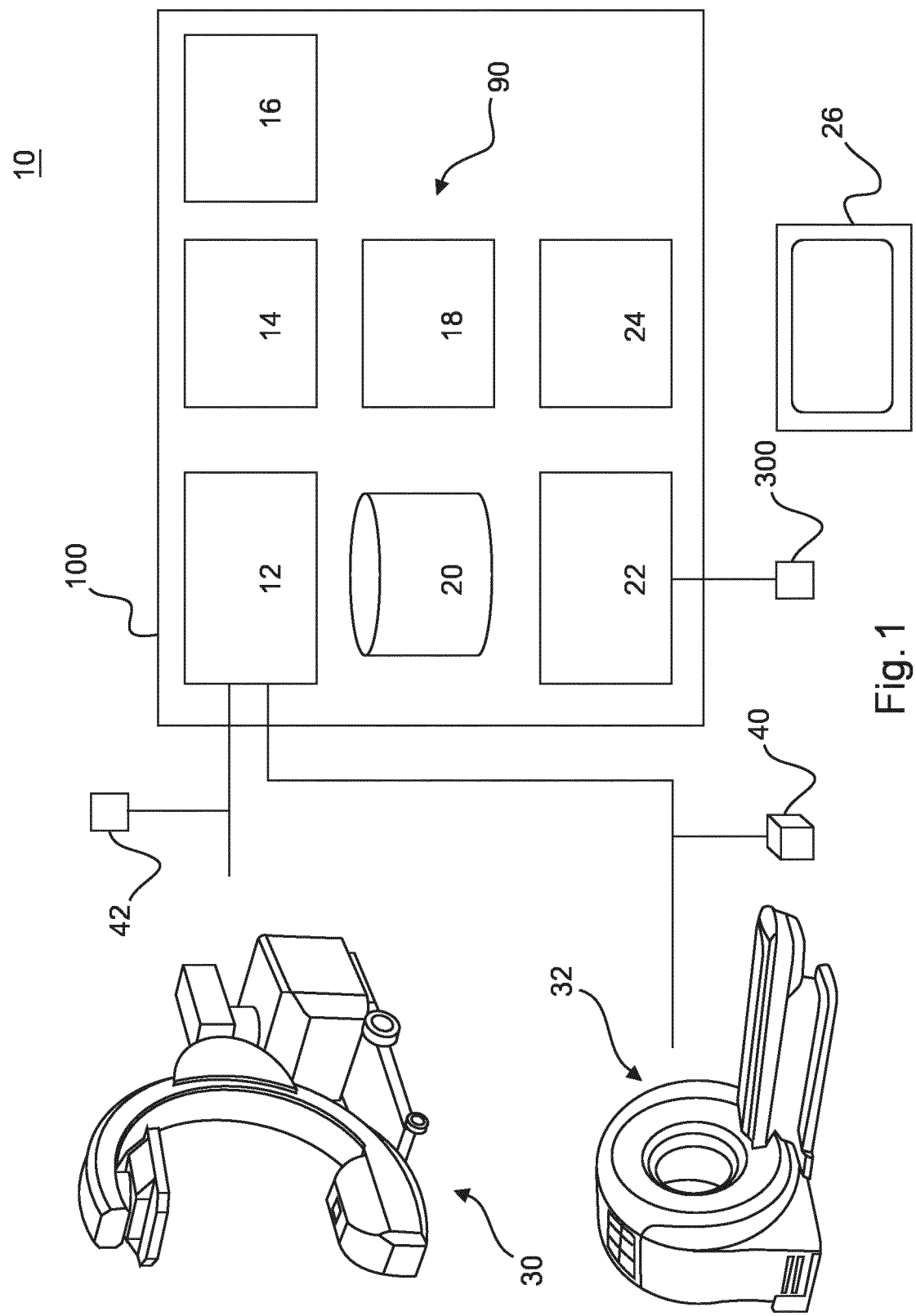
FIG. 1 is a schematic view of a vasculature modeling system including an image processing system, in accordance with various embodiments.

FIG. 1 is a schematic view of a vasculature modeling system 10 including an image processing system 100, a display device 26, a 2D image acquisition machine 30, a 3D image acquisition machine 32 and control modules 90, in accordance with various embodiments. The vasculature modeling system 10 is configured to build an enhanced 3D model based of a bodily vessel, e.g. an artery, by combining both 3D imaging data and 2D imaging data using a computer implemented enhanced 3D modeler that preserves 3D spatial information from the 3D imaging data, cross-sectional shape information form the 3D imaging data, diameter information from the 2D imaging data and imaging density from the 2D imaging data. In this way, positive aspects of both the 3D imaging data and the 2D imaging data are built into an enhanced 3D vessel model, which may provide a more accurate representation of the vessel as compared with a situation where a model is built either from 3D imaging data alone or from 2D imaging data alone.

Figure 2:
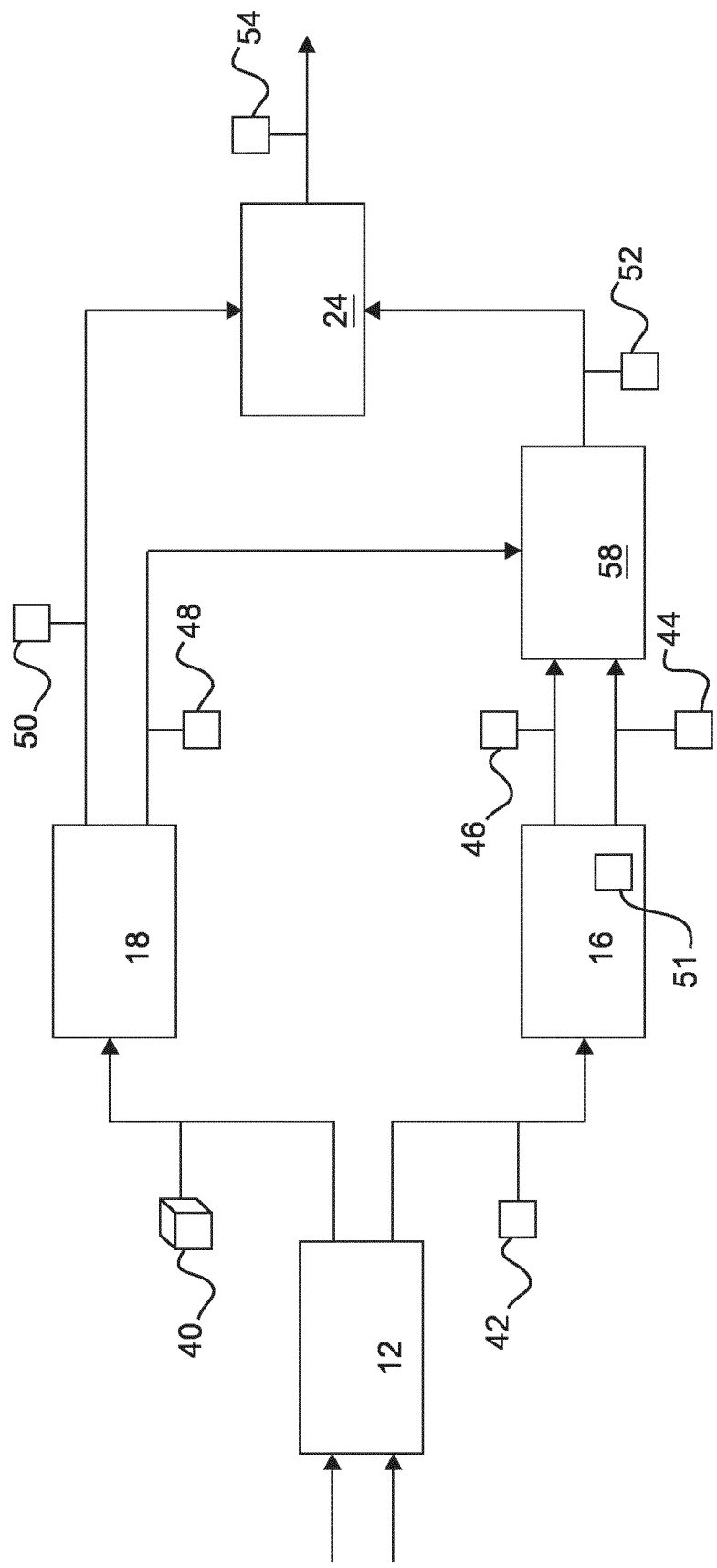
FIG. 2 is a first data flow diagram illustrating flow of data between various modules of the image processing system of FIG. 1, in accordance with various embodiments.

The 3D image acquisition machine 32 is configured for obtaining intrabody 3D imaging data. In one embodiment, the 3D image acquisition machine 32 obtains cross-sectional slice images of a patient and moves the patient and machine 32 relative to one another to obtain axially successive slices of the patient, thereby allow 3D imaging data 40 to be generated. In embodiments, the 3D image acquisition machine 32 generates 3D angiogram imaging data 40. It is envisaged that a body magnetic resonance imaging, MRI, machine is used or computed axial tomography, CAT, scanner is used as the image acquisition machine 32. As one example embodiment, FIG. 2 shows the case of a CAT machine 32. The CAT scanner is generally a box-like machine with a hole, or short tunnel, in the center. A patient lies on an examination table that slides into and out of the tunnel. An x-ray tube and x-ray detectors are located opposite each other in a ring, called a gantry, and rotate around the patient.

The image acquisition machine 30 is configured for generating 2D imaging data 42 of a patient. The image acquisition machine 30 is configured for X-ray imaging, in accordance with various embodiments. The image acquisition machine 30 is, in embodiments, configured for angiographic image acquisition. As such, the 2D imaging data 42 is 2D angiogram imaging data. In the illustrated embodiment, the image acquisition machine 30 includes a detector and a source. In a specific embodiment, the imaging acquisition machine 30 has a C-arm configuration, with the detector at one end of the C-arm and the source at the other end of the C-arm.

The display device 26 is any monitor, screen, or the like suitable for presenting a graphical user interface (GUI) capable of presenting an enhanced 3D model and results of a hemodynamic simulation as described herein.

The electrocardiogram sensor 70 is any sensor configured to provide a cardiac signal indicating a length of time of each cardiac cycle, i.e. heartbeat, and to identify timing of phases of the cardiac cycle.

In embodiments, the obtained 3D imaging data 40 and 2D imaging data 42 are provided to the image processing system 100 where various image processing operations are performed as will be described further herein, particularly with respect to FIGS. 2 to 4. Generally, the image processing system 100 is configured to build a 3D geometric model, e.g. a 3D vasculature model based on the 3D imaging data 40 (e.g. 3D angiography imaging data) and to build a 2D model, e.g. a 2D vasculature model, based on the 2D imaging data 42 (e.g. 2D angiography imaging data 42). The 3D vasculature (such as an artery model) model is, generally, at a coarser spatial resolution (such as of about 0.4 mm per voxel) than the 2D model (such as between 0.1-0.2 mm per pixel). The 3D model has eccentricity information and 3D geometry information, whilst the 2D model has more detailed spatial resolution and more accurate diameter information for the scanned vessels. The image processing system 100 is configured to combine the 3D geometric model and the 2D model and to generate an enhanced 3D model. The enhanced 3D model combines the advantages of high resolution of the 2D imaging data 42 with depth/geometry information from lower resolution 3D imaging data 40. In more detail, the enhanced 3D model is generated to preserve vessel eccentricity information and information on location in 3D space (e.g. centerline information) from the 3D model and spatial resolution and diameter information from the 2D model, as will be described in more detail herein. The image processing system is, in some embodiments, configured to run a hemodynamic simulation based on the enhanced 3D model and at least one hemodynamic value is derived from the simulation, such as pressure rations. The pressure ratios are more reliable due to the enhanced nature of the enhanced 3D model (e.g. so that the simulation can take into account eccentricity information from the 3D imaging data 40 and accurate diametric information from the 2D imaging data 42).

The image processing system 100 includes at least one processor 14 and a computer readable storage device, memory or media 20. The processor 14 can be any custom made or commercially available processor, a central processing unit (CPU), a graphics processing unit (GPU), an auxiliary processor among several processors associated with the image processing system 100, a semiconductor based microprocessor (in the form of a microchip or chip set), a macroprocessor, any combination thereof, or generally any device for executing instructions. The computer readable storage device, memory or media 20 may include volatile and nonvolatile storage in read-only memory (ROM), random-access memory (RAM), and keep-alive memory (KAM), for example. KAM is a persistent or non-volatile memory that may be used to store various operating variables while the processor 14 is powered down. The computer-readable storage device, memory or media 20 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the image processing system 100 in controlling the vasculature modeling system 10. The instructions are configured for executing the modules 90 of the image processing system 100 of FIG. 1, the data flow processes of FIGS. 2 and 3 and the methods of FIG. 4 as described further herein.

The instructions may include one or more separate programs, each of which comprises an ordered listing of executable instructions for implementing logical functions. The instructions, when executed by the processor 14, receive and process images from the image acquisition machines 30, 32, perform logic, calculations, methods and/or algorithms for automatically controlling modules 90 of the image processing system 100, and generate control signals to a hemodynamic simulator 22 and a display device 60. In particular, the instruction are operable to generate an enhanced 3D model combining higher spatial resolution of 2D imaging data 42 and eccentricity and centerline information from 3D imaging data 40, which is displaced on display device 26 and used in hemodynamic simulator 22 in various embodiments. Although only one image processing system 100 is shown in FIG. 1, embodiments of the vasculature modeling system 10 can include any number of image processing systems 100 that communicate over any suitable communication medium or a combination of communication mediums and that cooperate to process images, perform logic, calculations, methods, and/or algorithms, and generate control signals to automatically control features of the vasculature modeling system 10.

In various embodiments, the image processing system 100, such as a general-purpose computer, is operably connected to the image acquisition machines 30, 32 controls operation of the image acquisition machines 30, 32 for performing scans to obtain 3D imaging data 40 and 2D imaging data 42 and processes the imaging data 40, 42 from the image acquisition machines 30, 32. The processed images are, in some embodiments, presented on the display device 26 of the vasculature modeling system 10 in the form of an enhanced 3D model.

The image processing system 100 includes a number of modules 90 for executing the vasculature modeling systems 10, data flows and methods 200 described herein to receive 2D and 3D imaging data 40, 42, generate and combine 2D and 3D models to provide an enhanced 3D model and to display and/or perform a hemodynamic simulation on the enhanced 3D model. The modules 90 described herein include at least one processor 14, a memory 20 and computer program instructions stored on the memory 20 for implementing the various functions and processes described with respect to the modules 90. Although separate modules 90 are described herein for particular functions, this does not exclude an integrated topology. Further, the shown modules 90 may be divided into further sub-modules. The modules 90 are in communication with one another as necessary to implement the features, processes and systems described herein.

The modules 90 will be described additionally with respect to the data flow diagram of FIG. 2 as a first embodiment and with respect to the data flow diagram of FIG. 3 as a second exemplary embodiment to illustrate exemplary functions and effects of each module 90. Certain modules are common to both the first and second embodiments including the 3D modeler 18, the 2D modeler 16, the hemodynamic simulator 22, an enhanced 3D modeler 24 and a data receiver 12. These will be described first in so far as they have common functionality between the first and second embodiments before discussing specific aspects of each alternative exemplary implementation in FIGS. 2 and 3.

Data receiver 14 is configured to receive the 3D imaging data 40 and the 2D imaging data 42. The imaging data 40, 41 represents angiography of the patient in one embodiment. The data receiver 14 is configured to route the imaging data 40, 42 to various other modules of the image processing system 100 including 2D modeler 16 and 3D modeler 18.

The 2D modeler 16 and the 3D modeler 18 are configured to respectively generate a 2D model 51, 68 and a 3D model 50, 66 based respectively on the 2D imaging data 42 and the 3D imaging data 40. In embodiments, the 2D imaging data 42 and the 3D imaging data 40 are obtained by the image acquisition machines 30, 32 in the same examination interval and, in some embodiments, are at the same cardiac state. The modelers 16, 18 are configured to compute the geometric vasculature (e.g. artery) models 50, 51, 66, 68 with any manual or automatic segmentation approach. Exemplary model computation methods are described in Lesage, D., Angelini, E. D., Bloch, I., & Funka-Lea, G. (2009). A review of 3D vessel lumen segmentation techniques: Models, features and extraction schemes. Medical image analysis, 13(6), 819-845. Vessel segmentation and modeling through modelers 16, 18 is, per se, known to the skilled person.

The enhanced 3D modeler 24 differs in exemplary specifics for the first and second embodiment of FIGS. 2 and 3 as will be described below, but there are some common features. The enhanced 3D modeler 24 is configured to generate an enhanced 3D model 54. The enhanced 3D modeler 24 is configured, in some embodiments, to derive geometric data or features from the 2D model 51, 68 and the 3D model 50, 66 in order to generate the enhanced 3D model 54. In one example, the enhanced 3D modeler 24 is configured to operate a model generation algorithm that includes one or more terms or constraints such that at least at least one of the following data items is preserved in the enhanced 3D model 54: information on diameters coming from the 2D imaging data 40, shape cross-section coming from the 3D imaging data 42 (e.g. eccentricity data on the vessel cross section), spatial resolution of the 2D imaging data 42 and 3D vessel location data (e.g. centerline data) from the 3D imaging data 40. Such constraints are built into modeling code for the enhanced 3D modeler 24, in some embodiments.

The hemodynamic simulator 22 is configured to receive the enhanced 3D model 54, to run a hemodynamic simulation and to derive from the hemodynamic simulation hemodynamic data value(s) 300. The hemodynamic data value(s) 300 are pressure ratios across a stenosis, in one embodiment, for classification of vessel disease such as coronary artery disease. For example, the hemodynamic data value(s) 300 are fraction flow reserve value(s) corresponding to estimated pressure differences across a coronary artery stenosis. Any hemodynamic simulation is able to be performed that simulates blood flow in the enhanced 3D vasculature model 54 including simulating variable flow profiles in eccentric vessel segments. The hemodynamic simulator 22 is, in one embodiment, configured to run a computation fluid dynamics algorithm to simulate blood flow in the enhanced 3D model 54. One example hemodynamic simulation is disclosed in VioMed Research International, Volume 2014 (2014), Article ID 514729, Numerical Simulation and Clinical Implications of Stenosis in Coronary Blood Flow by Jun-Mei Zhang et al.

In embodiments, a contrast injection takes place such that certain images 102 will be contrast enhanced images 103. That is, a sequence of images 104 within the stream of images 102 will be contrast enhanced images 104. The transient nature of the contrast injection means that neighboring images 102 received before the contrast enhanced images 104 and neighboring images 102 received after the contrast enhanced images 104 are not contrast enhanced. However, a group of uninterrupted contrast enhanced images 104 are identifiable for the purpose of illuminating vessels. The contrast agent is, in various embodiments, injected through a catheter of the interventional tool 44 from which a balloon implement, a guide wire or other implement movable extends. The contrast agent is, in accordance with an exemplary embodiment, injected using a pump that is controlled by a gated contrast agent controller 64 for ensuring that the contrast agent injection lasts for at least one heartbeat.

Contrast agent detector 20 is configured to receive each image of the stream of images 102 and to automatically detect contrast enhanced images 104 within the images 102, or a defined portion thereof. The contrast agent detector 20 groups those images 104 that have been identified as including contrast agent and pass the contrast enhanced images 104 to the image extractor 22. Accordingly, contrast agent detector 20 is configured to identify image frames 104 that containing contrast agent, and to group them into a temporal cluster representing a contrast agent puff. The contrast agent detector 20 can be considered an image filter that allows contrast enhanced images 104 to pass and that removes images 102 that are not identified as being contrast enhanced.

There are various possibilities for automatically detecting contrast enhanced images 104. Generally, the contrast agent detector 20 is configured to use an image processing technique to identify contrast enhanced images 104. One possibility is to monitor image at least one parameter that either indicates presence of contrast agent in the image (such as a mean brightness of the image, or a surface of the image whose brightness is under a defined percentage, e.g. 20%, of a maximum brightness), or that indicates a visibility of vessels in the image (such as a mean ridgeness of the image, wherein ridgeness is a response to an elongated filter that enhances vessels). An increase of the at least one parameter, e.g. an increase beyond a predetermined threshold, is used to indicate that images meeting this requirement are contrast enhanced images 104. Another possibility is to use an image processing technique including detecting vessel segments in each frame of an image sequence and to determine a score vector for the fluoroscopic image sequence based on the detected vessel segments in each frame of the fluoroscopic image sequence. A contrast agent injection is determined to be present in the fluoroscopic image sequence based on the score vector. Further information on this possibility is found in US2012230558. Other possibilities include using deep-learning by training a neural network to identify contrast enhanced images 104 from non-contrast enhanced images.

Having discussed general features of the modules 90 of the image processing system 100, exemplary detailed implementations for first and second embodiments will be described.

In the exemplary first embodiment of FIG. 2, a quasi 3D modeler 58 is incorporated into the modules 90. The quasi 3D modeler 58 is configured to receive the 2D model itself or data 44, 46 derived from the 2D model 51. Quasi 3D modeler 58 is configured to receive data 48 derived from the 3D model 50.

The quasi 3D modeler 58 is configured to generate a quasi 3D model from data 44, 46 and/or from the 2D model 51 and to register a centerline, e.g. based on centerline data 44, from the 2D model 51 with a centerline, e.g. based on 3D centerline data 48, from the 3D model to deform the 2D centerline 44 to follow a 3D path based on the 3D centerline 48. The quasi 3D modeler 58 is configured to combine the registered centerline with diameter/radius data 46 from the 2D model to generate a quasi 3D model 52. The quasi 3D model 52 is at the spatial resolution of the 2D imaging data 42/the 2D model 51 and includes accurate radius/diameter data from the 2D imaging data 42/the 2D model 51 at the higher spatial resolution. Further, the quasi 3D model 52 includes 3D position data (based on the centerline data 48) from the 3D model. The quasi 3D model 54 takes an assumption of circular cross-sections for each diameter reading in the 2D diameter data 46.

In the exemplary first embodiment of FIG. 2, the enhanced 3D modeler 24 is configured to deform a cross-sectional profile of the quasi 3D model 52 to match or substantially match the cross-sectional profile 3D model 50 from the 3D modeler 18, whilst including a constraint (regularization term) to minimize change of the diameters of the quasi 3D model 52. In this way, an enhanced 3D model 54 is generated at the spatial resolution of the 2D model 51, having diameters from the 2D model 51, having eccentricity from the 3D model 50 and following the centerline from the 3D model 50. In embodiments, the enhanced 3D modeler 24 is configured to use a 3D-3D registration and deformation image processing procedure on the quasi 3D model 52 and the 3D model 50 with local cross-section shape deformations and with a regularization term controlling the cross-sectional shape deviations on the quasi 3D model 52. A goal of the enhanced 3D modeler 54 is to deform the quasi 3D model 52 so that its cross sectional shapes are more consistent with information given by the 3D model 50 but without changing too much the diameter values coming from the 2D model 51. In one exemplary embodiment, the registration and deformation procedure is expressed in a variational framework (energy minimization equation) with a specific term (regularization term) that allows control of the degree of diameter changes.

Figure 3:
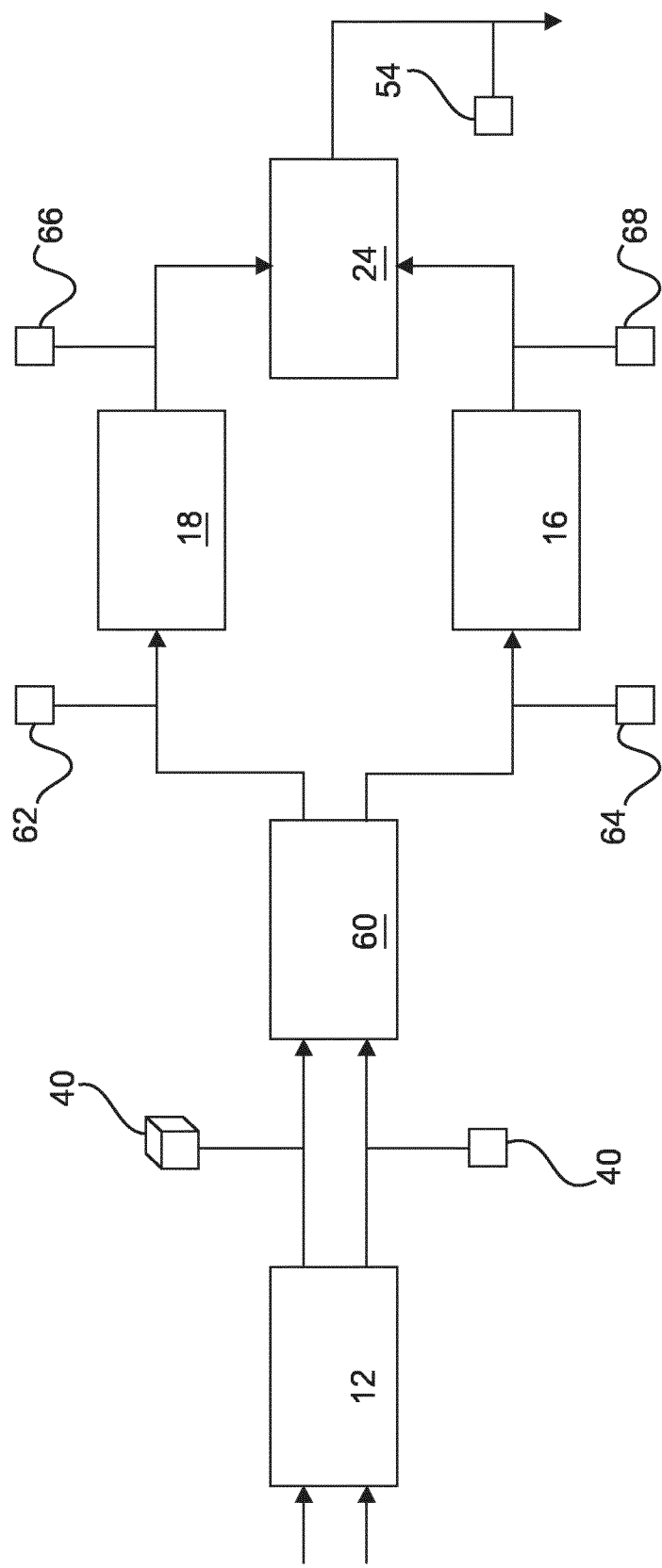
FIG. 3 is a second data flow diagram illustrating flow of data between various modules of the image processing system of FIG. 1, in accordance with various embodiments

In the exemplary second embodiment of FIG. 3, the modules 90 include a registration module 60 configured to perform an image registration procedure on the 2D imaging data 42 and the 3D imaging data 40 to produce registered 3D imaging data 62 and registered 2D imaging data 64. The registration procedure is a non-rigid (i.e. elastic) registration image processing algorithm. There are many ways to perform 3D and 2D registration in the registration module 60 as discussed in Med Image Anal. 2012 April; 16(3):642-61, A review of 3D/2D registration methods for image-guided interventions by Markelj et al.

The 2D and 3D modelers 16, 18 are configured to operate on the registered 2D imaging data 64 and the registered 3D imaging data 62, respectively, to produce registered 2D and 3D models 66, 68. The modelers 16, 18 are configured to run image segmentation processes, for example as has been described heretofore. In embodiments, the 3D modeler is configured to build the registered 3D model 66 at the same resolution as the registered 2D model 68. Increasing the resolution of the registered 3D model 66 is performed by using an image resolution modifying algorithm. For example, in the case of a mesh type 3D model, a mesh density is set to be higher than the resolution of the 3D imaging data 40 to match the resolution of the 2D imaging data.

The enhanced 3D modeler 24 is configured to deform the registered 3D model 66 to fit the registered 2D model 68 (or vice versa). The deformation procedure run by the enhanced 3D modeler 24 includes regularization terms or constraints so that the enhanced 3D model 54 is generated having spatial resolution of the 2D model 68 (since the 3D model 66 is constructed at that resolution), having diameters of the 2D model 68, having cross-section shape (e.g. eccentricity) from the 3D model 66 and being 3D spatially registered (e.g. having a vessel centerline from the 3D imaging data 40) according to the 3D model. In this way, advantageous aspects of the 2D and 3D imaging modalities are integrated in the enhanced 3D model 54.

Figure 4:
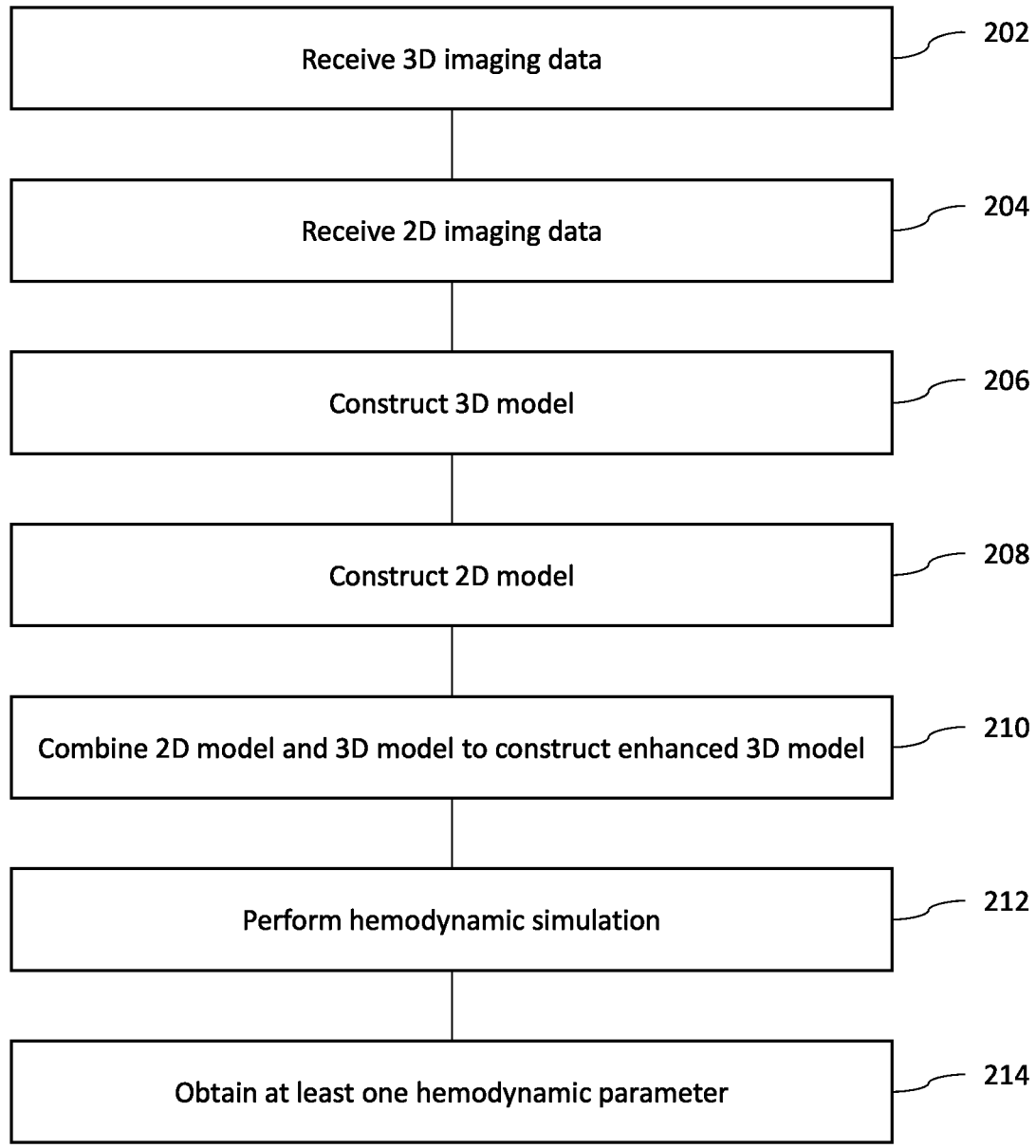
FIG. 4 is a flow chart illustrating a computer implemented method for vasculature modeling, in accordance with various embodiments.

Referring now to FIG. 4, and with continued reference to FIGS. 1 to 3, a flowchart illustrates a computer implemented method 200 for vasculature modeling that can be performed by the vasculature modeling system 10 of FIG. 1 in accordance with the present disclosure. As can be appreciated in light of the disclosure, the order of operation within the method is not limited to the sequential execution as illustrated in FIG. 4, but may be performed in one or more varying orders as applicable and in accordance with the present disclosure. In various embodiments, the method 200 can be scheduled to run based on one or more predetermined events, and/or can run continuously during operation of the vasculature modeling system 10.

The computer implemented method 200 includes a step 202 of receiving 3D imaging data 40. The 3D imaging data 40 is generated by the 3D image acquisition machine 32. The 3D imaging data 40 is MRI or CT angiography imaging data in various embodiments. The computer implemented method 200 includes a step 204 of receiving 2D imaging data 42. The 2D imaging data is generated by the 2D image acquisition machine 30. The 2D imaging data 42 is angiography imaging data in various embodiments. The 2D imaging data 42 is at a higher (finer) spatial resolution than the 3D imaging data 40. The receiving steps 202, 204 are performed through the data receiver 12. In embodiments, a single vessel level is included in the received imaging data 40, 42 or an artery tree is included. The received imaging data 40, 42 starts and ends end at the same positions or is cropped to do so.

The computer implemented method 200 includes a step 206 of constructing a 3D model 50, 66. The computer implemented method 200 includes a step 208 of constructing a 2D model 51, 68. The steps 206, 208 are performed through 2D and 3D modelers 16, 18. The models 50, 51, 66, 68 are constructed using image segmentation processes to extract at least one vessel of interest.

In step 210, the 2D model 51, 68 and the 3D model 50, 66 are combined to construct an enhanced 3D model 54. The combination step is performed by the image processing system 100 including at least the enhanced 3D modeler 24. The enhanced 3D model 54 is generated using image deformation procedures based on the 2D model 51, 68 and the 3D model 50, 66 that include regularization terms configured to maintain diameter data of the vessel(s) from the 2D imaging data 42/model 51, 68, to maintain spatial resolution of the 2D imaging data 42/model 51, 68, to maintain cross-section shape (e.g. eccentricity) of the vessel (s) of the 3D model 50, 66 and/or to maintain spatial location of vessel(s) of the 3D model 50, 66.

In a first exemplary embodiment as has been described with reference to FIG. 2, step 210 includes transforming the 2D model 51 into a quasi 3D model 52 by registering 2D centerline 44 from the 2D model 51 to the 3D centerline 48 from the 3D model 50 and using diameters from the 2D model 51 as circular sections along the registered 2D centerline. Further, step 210 includes registering the quasi 3D model 51 and the 3D model 50 to construct the enhanced 3D model 54. The registration process may be carried out using a 3D-3D registration procedure with local deformations and with a regularization term controlling the shape deviation of the quasi 3D model 52.

In a second exemplary embodiment as has been describe with reference to FIG. 3, step 210 includes registering the 3D imaging data 40 and the 2D imaging data 42 using a non-rigid deformation prior to steps 206, 208 of building 2D and 3D models 66, 68. Further, the 2D vessel model 68 and the 3D vessel model 66 are combined to get the enhanced 3D model 54 by deforming the 3D model 66 to fit to the 2D model 68.

The computer implemented method 200 includes a step 212 of performing hemodynamic simulation. Step 212 is carried out through hemodynamic simulator 22. The hemodynamic simulation includes running computed fluid dynamics simulation. The simulation results in obtaining at least one hemodynamic parameter in step 214. In embodiments, the hemodynamic parameter is a fraction flow reserve, FFR, measurement at a stenosis.

The enhanced 3D model 54 is able to provide more realistic hemodynamic values as it takes into account more information than a model coming only from only one of 2D imaging and 3D imaging. Furthermore, a more intuitive 3D visualization of the vessel model 54 (e.g. with correct 3D curvatures) is available through display device 26. Yet further, the enhanced 3D model 54 provides hemodynamic properties (e.g. variable flow profiles in eccentric vessel segments), which is not possible if only a 2D projection of the vessel is used.

In another exemplary embodiment of the present invention, a computer program or a computer program element is provided that is characterized by being adapted to execute the method steps of the method according to one of the preceding embodiments, on an appropriate processing system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a

The invention claimed is:

1. A vasculature modelling system, the system comprising:
one or more processors configured to:
receive two dimensional (2D) imaging data including a region of interest of vasculature, wherein the 2D imaging data is obtained by a first image acquisition device;
determine, based on the 2D imaging data, a plurality of vessel diameters along a first vessel centerline;
receive three dimensional (3D) imaging data of the region of interest, wherein the 3D imaging data is obtained by a second image acquisition device;
determine, based on the 3D imaging data, a plurality of second cross-sectional shapes defining a second profile of the region of the interest along a second vessel centerline;
generate an enhanced 3D model of the region of interest; and
output the enhanced 3D model to a display in communication with the one or more processors,
wherein, to generate the enhanced 3D model, the one or more processors are configured to:
build a quasi 3D model based on the 2D imaging data, wherein the quasi 3D model comprises a plurality of first cross-sectional shapes defining a first profile of the region of interest along the first vessel centerline, wherein the plurality of first cross-sectional shapes are a plurality of circles, and wherein each first cross-sectional shape of the plurality of first cross-sectional shapes comprises a corresponding vessel diameter of the plurality of vessel diameters; and
deform the quasi 3D model into the enhanced 3D model,
wherein, to deform the quasi 3D model into the enhanced 3D model, the one or more processors are configured to deform the plurality of circles to be the plurality of second cross-sectional shapes.

2. The vasculature modelling system of claim 1, wherein a spatial resolution of the 2D imaging data is greater than a spatial resolution of the 3D imaging data.

3. The vasculature modelling system of claim 1, where the one or more processors are configured to generate the enhanced 3D model of the region of interest having a spatial resolution of the 2D imaging data.

4. The vasculature modelling system of claim 1, wherein the one or more processors are configured to generate the enhanced 3D model of the region of interest by combining the 3D imaging data and the 2D imaging data using an image registration and image deformation technique including terms to maintain, in the enhanced 3D model, at least one of:
the second vessel centerline based on vessel centerline data;
the plurality of second cross-sectional shapes;
a spatial resolution derived from the 2D imaging data; or
the plurality of vessel diameters based on vessel diameter data derived from the 2D imaging data.

5. The vasculature modelling system of claim 1, wherein at least one of:
the 3D imaging data is magnetic resonance imaging (MRI) imaging data or computed tomography (CT) imaging data, or
the 2D imaging data is angiogram imaging data.

6. The vasculature modelling system of claim 1, the one or more processors are configured to:
perform a hemodynamic simulation using the enhanced 3D model; and
derive at least one hemodynamic parameter based on the hemodynamic simulation.

7. The vasculature modelling system of claim 1, wherein the one or more processors are configured to perform 2D to 3D image registration process based on the 2D imaging data and the 3D imaging data to produce registered 2D and 3D imaging data and to perform an image deformation process based on the registered 2D and 3D imaging data.

8. The vasculature modelling system of claim 1, wherein the one or more processors are further configured to:
determine the first vessel centerline based on the 2D imaging data, wherein the first vessel centerline comprises a 2D path; and
determine the second vessel centerline based on the 3D imaging data, wherein the second vessel centerline comprises a 3D path,
wherein the quasi 3D model comprises the first vessel centerline, and
wherein, to deform the quasi 3D model into the enhanced 3D model, the one or more processors are further configured to deform the first vessel centerline to have the 3D path of the second vessel centerline.

9. A computer implemented method for vasculature modelling, the method comprising:
receiving two dimensional (2D) imaging data including a region of interest of vasculature, wherein the 2D imaging data is obtained by a first image acquisition device;
determining, based on the 2D imaging data, a plurality of vessel diameters along a first vessel centerline;
receiving three dimensional (3D) imaging data of the region of interest, wherein the 3D imaging data is obtained by a second image acquisition device;
determining, based on the 3D imaging data, a plurality of second cross-sectional shapes defining a second profile of the region of the interest along a second vessel centerline;
generating an enhanced 3D model of the region of interest, wherein the generating comprises:
building a quasi 3D model based on the 2D imaging data, wherein the quasi 3D model comprises a plurality of first cross-sectional shapes defining a first profile of the region of interest along the first vessel centerline, wherein the plurality of first cross-sectional shapes are a plurality of circles, and wherein each first cross-sectional shape of the plurality of first cross-sectional shapes comprises a corresponding vessel diameter of the plurality of vessel diameters; and
deforming the quasi 3D model into the enhanced 3D model, wherein the deforming comprises deforming the plurality of circles to be the plurality of second cross-sectional shapes; and
outputting the enhanced 3D model to a display in communication with the one or more processors.

10. The computer implemented method of claim 9, further comprising performing a hemodynamic simulation on the enhanced 3D model and deriving a hemodynamic parameter from the hemodynamic simulation.

11. The computer implemented method of claim 9, wherein the generating uses an image registration and image deformation process that includes maintaining, in the enhanced 3D model, at least one of:

the second vessel centerline based on vessel centerline data derived from the 3D imaging data;
the plurality of second cross-sectional shapes;
a spatial resolution derived from the 2D imaging data; or
the plurality of vessel diameters based on vessel diameter data derived from the 2D imaging data.

12. A computer program element adapted to implement an image processing system or adapted to perform the method steps of claim 9 when executed by at least one processor.

* * * * *